United States Patent [19]

Darrel et al.

[11] 4,429,578

[45] Feb. 7, 1984

[54] ACOUSTICAL DEFECT DETECTION SYSTEM

[75] Inventors: Bernard Darrel; Joseph Czechowski, III, both of Schenectady, N.Y.

[73] Assignee: General Electric Company, Schenectady, N.Y.

[21] Appl. No.: 360,293

[22] Filed: Mar. 22, 1982

[51] Int. Cl.³ .................. G01H 1/00; G01M 7/00; G01N 29/04
[52] U.S. Cl. ........................ 73/659; 73/660; 340/680; 340/683
[58] Field of Search .............. 73/659, 660; 340/680, 340/682, 683

[56] References Cited

U.S. PATENT DOCUMENTS

| | | | |
|---|---|---|---|
| 3,677,072 | 7/1972 | Weichbrodt et al. | 73/67 |
| 3,705,516 | 12/1972 | Reis | 73/660 |
| 3,712,130 | 1/1973 | Weichbrodt et al. | 73/162 |
| 3,913,084 | 10/1975 | Bollinger et al. | 73/660 |
| 4,213,346 | 7/1980 | Polovnikov et al. | 73/660 |
| 4,335,600 | 6/1982 | Wu et al. | 73/660 |
| 4,352,293 | 10/1982 | Kurihara et al. | 73/660 |

OTHER PUBLICATIONS

Electronics, vol. 45, No. 23, Nov. 6, 1972, p. 33.

*Primary Examiner*—Howard A. Birmiel
*Attorney, Agent, or Firm*—Donald R. Campbell; James C. Davis, Jr.; Marvin Snyder

[57] ABSTRACT

The vibration of a moving device which has repetitive movements, for instance a rotary compressor, are sensed at the outer case and analyzed in real time in both the time and frequency plane. For the time analysis the envelope of the signal is generated; for the frequency analysis a fast Fourier transform is performed and separate power spectra for fractions of a revolution are produced. The signatures are compared with those of an acceptable device to identify rejects and abnormalities at a particular position of a moving part.

15 Claims, 8 Drawing Figures

ACOUSTICAL DEFECT DETECTION SYSTEM

BACKGROUND OF THE INVENTION

This invention relates to a diagnostic system and non-intrusive method of detecting internal defects in moving devices such as rotating and oscillating apparatus.

Rotary compressors used in room air conditioners have exceptionally light tolerances, in some cases only a few ten-thousandths of an inch. In addition they are hermetically sealed and therefore prone to early failure if small particles are present or introduced during assembly. When the compressor contains clean, correctly dimensioned parts and is properly assembled, normal noises are generated internally. Changes in these sounds indicate that the compressor is abnormal.

Some of these defects can be found by a trained operator but are subject to human interpretation. The pass-fail criteria vary between operators and also from day to day with the same operator. Some of the defects cannot be found by any operator. It was impossible to discover some small particles of hardened material that shorten life.

The warranty period for a compressor is five years and it is expensive to repair in the field. This invention is more sensitive than a human operator and the acceptance criteria are consistent. It is capable of performing an inspection at one test station that would require more than one station using more conventional methods.

SUMMARY OF THE INVENTION

The vibrations of rotary and oscillatory apparatus, and other devices which have repetitive movements, are analyzed in both the time and frequency plane. Each type of analysis is useful for a particular type of signature and the two in combination are more effective in detecting defects and their location. The sensor preferably is on the outer case of the apparatus. The conditioned signal is processed to produce a time signature which is related to device position and is the envelope (peak values vs. time) of the signal, and to produce a set of frequency signatures which are the power spectra for fractions of a cycle of movement. These signatures are compared with those of an acceptable device to identify abnormalities in vibration at a particular position of a moving part.

An illustrative diagnostic system for inspecting a rotary device such as a compressor performs the time and frequency analysis in real time. The signal conditioner filters out low frequency noise and high frequency components that could result in aliasing errors. Means are provided to generate a position reference once per revolution to synchronize averaging. The first analysis means is comprised of a rectifier and peak follower. The second analysis means has a fast Fourier transform device, means for squaring its output to yield each power spectra, and means for determining and subtracting the DC offset of this output. Separate spectra, say for each 1/16 of a revolution, prevents loud noises such as valving actions from masking defects at other rotational positions. The comparison of the time and frequency signatures with reference data of an acceptable compressor is performed in a computer.

The technique is nonintrusive, detects defects not found by conventional techniques, and removes variations in judgment that are typical of manual inspection.

DESCRIPTION OF THE PREFERRED EMBODIMENTS

Figure 1:
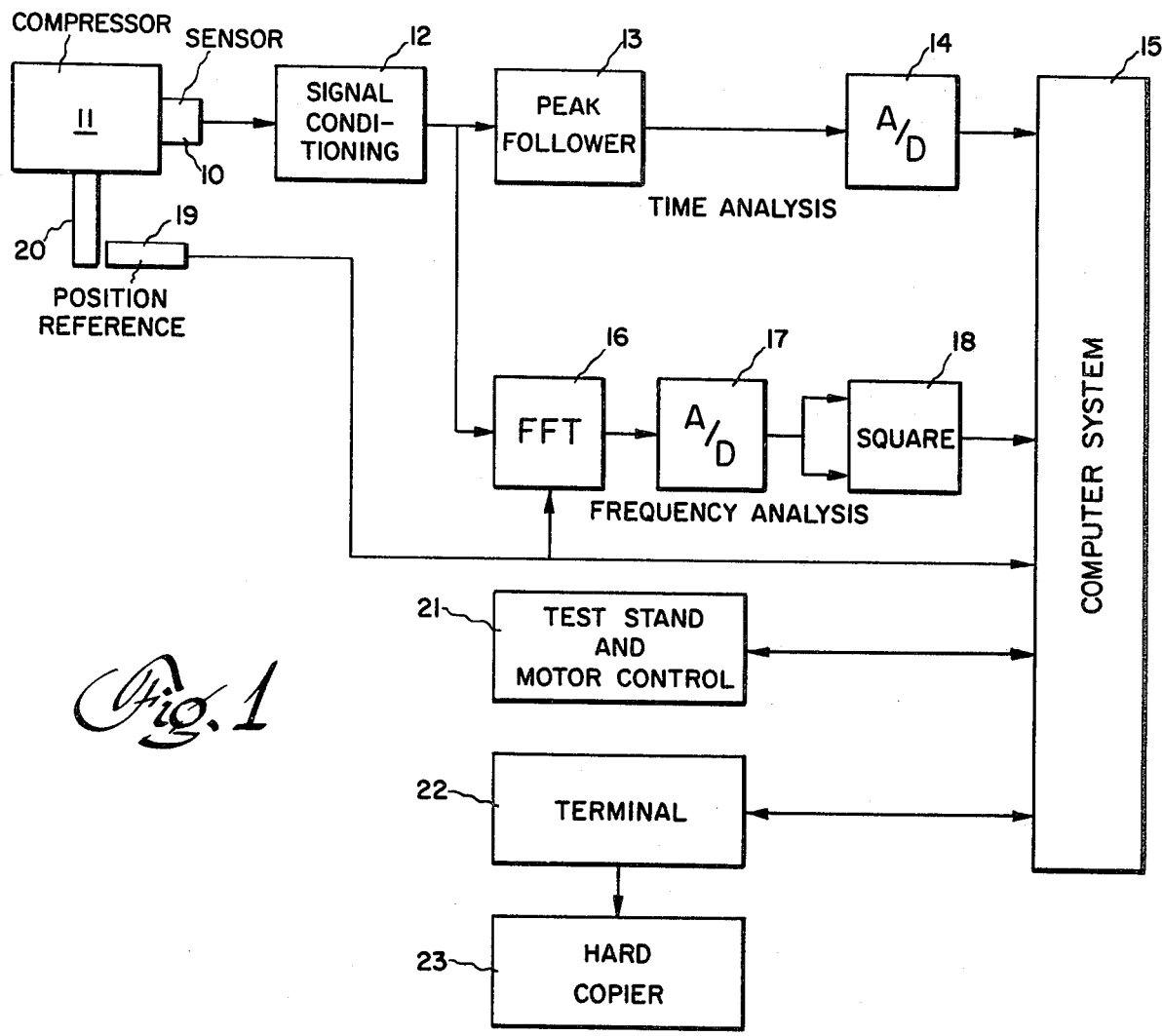
FIG. 1 is a simplified block diagram of a compressor diagnostic system.

Referring to FIG. 1, the analysis performed by the diagnostic system uses both the frequency and the time plane. Each of type of analysis is useful for a particular type of signature. If two events occur simultaneously but contain different frequency components, they can be separated in the frequency plane. If there is a small signal buried in random noise or if two events with the same frequency content occur separately in time, they are more easily detected by time averaging. An accelerometer or other vibration sensor 10 on the outer case of the compressor 11 generates an electrical signal representative of the mechanical and acoustic vibrations of the compressor. The sensor signal is presented to signal conditioning circuitry 12 where it is amplified and filtered before splitting in two directions for time and frequency analysis. For the time analysis the signal is rectified and fed to a peak follower 13, the envelope of the signal is generated, digitized in an analog-to-digital converter 14, and analyzed in the computer system 15. For the frequency analysis, a fast Fourier transform is also performed, and the power spectrum analyzed in the computer. The power spectra are generated at high speed using commercially available hardware systems. A fast Fourier transform device 16 has an analog output voltage which represents the equivalent signal level in the bandwidth. This output voltage is digitized in an analog-to-digital converter 17 and fed to a squaring circuit 18, and the result is sent to the computer. Separate spectra are calculated for equal fractions of a revolution, such as 1/16 of a revolution. This prevents loud noises produced by valving actions from masking defects that occur during other rotor angle positions. The frequency analysis is divided into sixteen rotor position segments. Some are comparatively noisy, others quiet. If the noise level were equally distributed this increases the sensitivity by 16. Since it is not equally distributed the improvement in sensitivity can be 2 to 3 orders of magnitude particularly in that part of the process that is normally quiet.

Both time and frequency are averaged sixteen times to improve the signal-to-noise ratio. A position reference signal is generated once per revolution by a device such as a magnetic sensor 19 which senses a slot in the end of the compressor shaft 20. This is fed to the FFT 16 and computer 15, and is used to synchronize the averaging of the data so that the analysis is always started at the same angular position of the shaft and is referenced to rotor position. The computer analyzes the preprocessed data and inspects the results. The test stand and motor which drives the compressor are controlled (see block 21) by the computer. A video terminal 22 is used for program selection, modification, and output display. A hard copier 23 is available to make a permanent record of anything displayed on the material.

Figure 2:
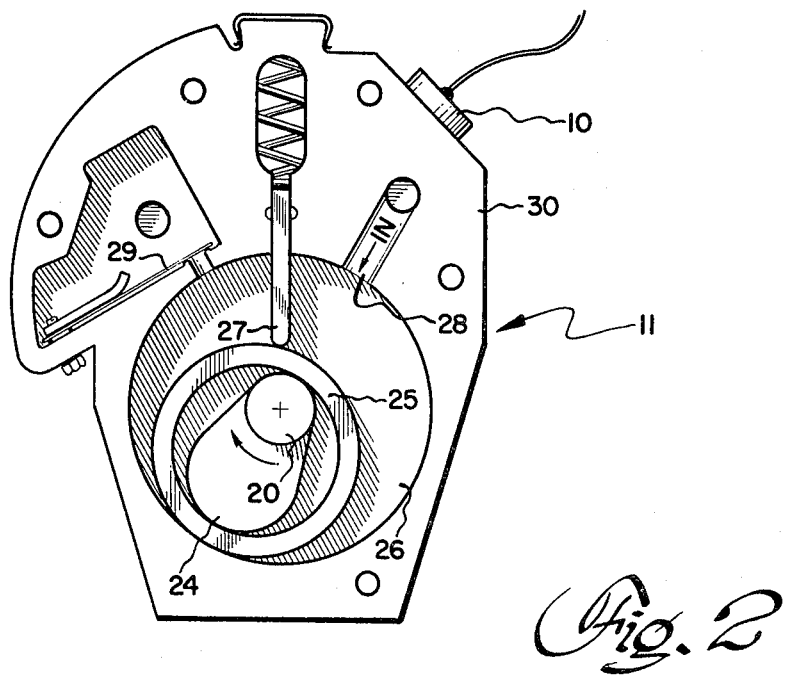
FIG. 2 is a sketch of internal components of a compressor which is inspected.

A typical room air conditioner compressor, which is also known as a pump, is illustrated in FIG. 2 with the cover removed. It is tested before attaching the drive motor and sealing them in a container. The shaft 20 and a cam 24 drive a cylinder 25 which is pressed against the wall of chamber 26 by a spring loaded vane 27 as it rotates. The refrigerant inlet 28 is sealed by the rotating cylinder, and the gas is compressed and discharged through a port when the spring type exhaust valve 29 opens. Structure-borne mechanical vibrations are sensed by the accelerometer 10 which is held against the outer case 30 of the pump by pneumatic pressure.

One common defect is leaving out an operation, for instance, forgetting to drill a relief hole. This changes the signature generated by the accelerometer; there is increased pressure and the flow noise produced when the exhaust valve opens is higher. Another common defect is that there is foreign material inside the pump. The harder material, such as that of which the vane is made, grinds away at the softer material, and in time the debris builds up and the pump can stall.

The acceptance criteria are based on a comparison of the time and frequency signatures with those of an acceptable compressor. Since a very large majority of the units last longer than the warranty period, statistical data can be taken. A sample of units are tested and their signatures statistically averaged. Since the rejection rate is known, that percentage of units whose signatures are furthest from the normal are removed from the sample. All subsequent units are tested using the statistically derived data. Each model has its own set of reference data, and as new models are introduced and old models redesigned, a new set of criteria is rapidly generated. This invention can be applied to devices other than rotary compressors, and used to diagnose problems in any moving device where the movements are repetitive including oscillating and rotary apparatus.

Figure 3:
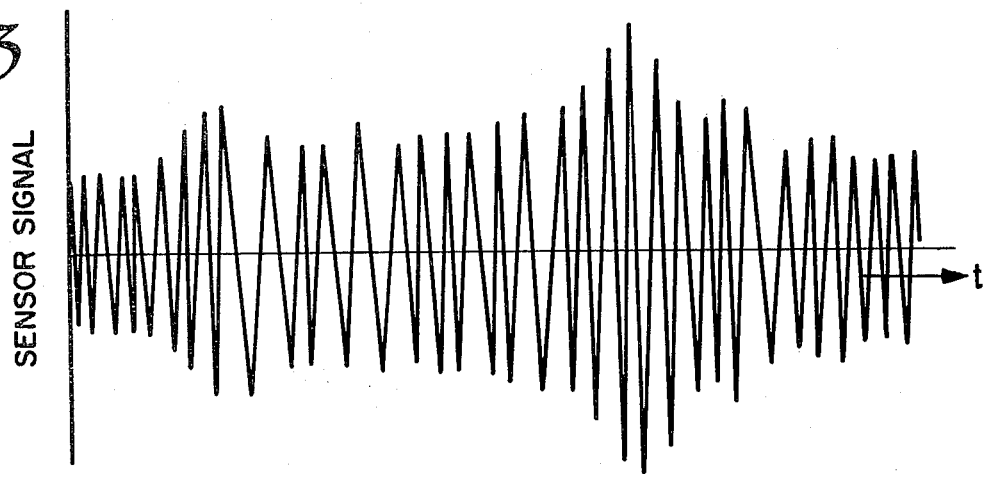
FIG. 3 shows the vibration signal generated by the sensor.
Figure 4:
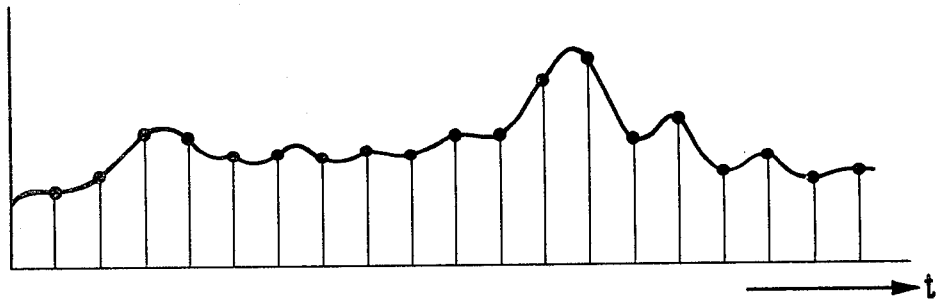
FIG. 4 depicts the envelope of the sensor signal which is sampled at equal time intervals.
Figure 7:
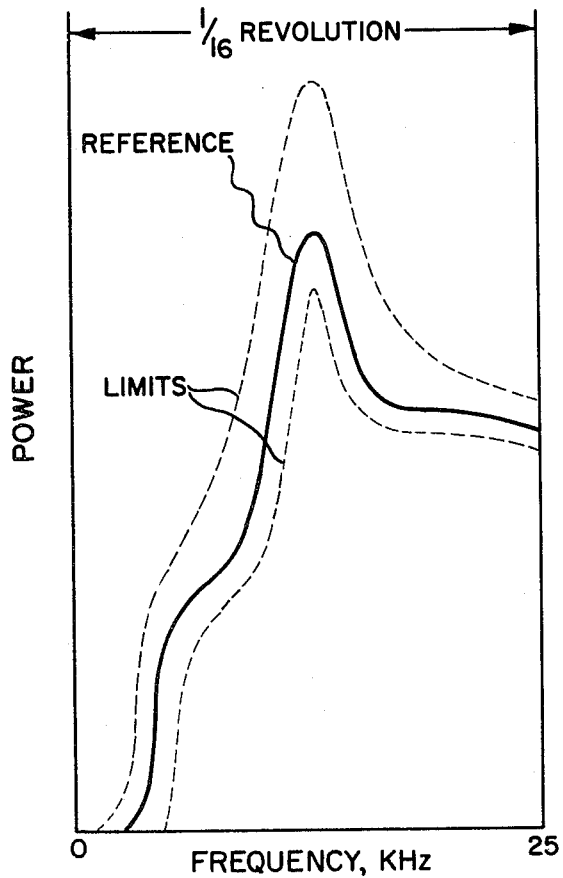
FIG. 7 has one frequency signature drawn to an enlarged scale and the allowable limits of acceptability.
Figure 5:
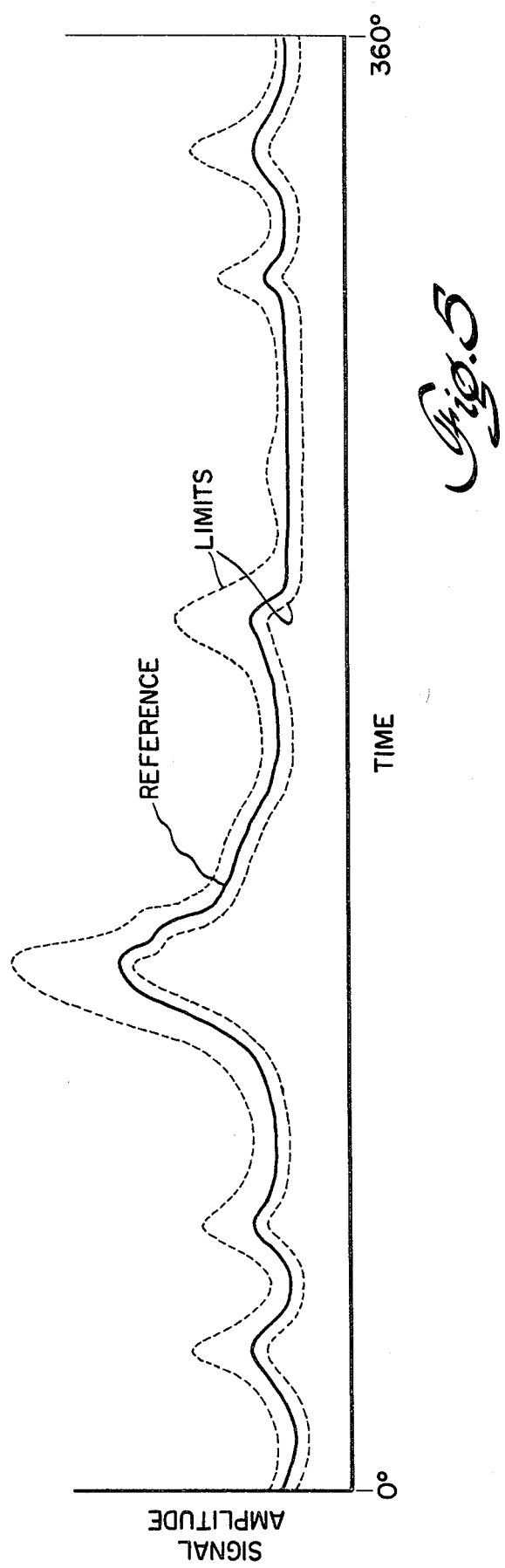
FIG. 5 shows a reference time plane signature and the allowable limits of an acceptable device.
Figure 6:
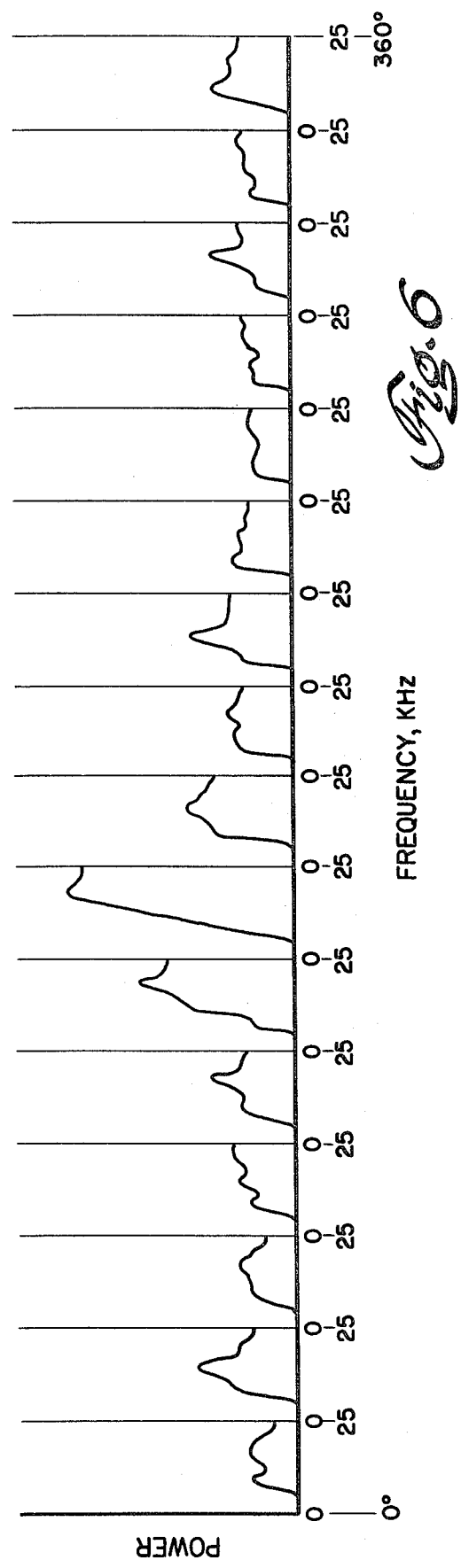
FIG. 6 shows a set of frequency signatures for one complete revolution.

FIG. 3 shows the signal generated by sensor 10 which corresponds to the vibrations of the pump. The signal is filtered to reject low frequency extraneous noise and high frequency components that could cause aliasing errors; the frequency band of the conditioned signal is 4-25 KHz in one system that was built. FIG. 4 shows the envelope of the rectified signal and sampling points at equal time intervals. While the peak value data for one revolution may be the time signature of the device under test, ordinarily many revolutions or cycles of movement are averaged. The time and frequency signatures of an acceptable device are drawn in FIGS. 5 and 6 as solid line curves but are actually stored in the computer system 15 in digital form. The signatures are related to rotor position. There is one time signature for one complete revolution, but there are sixteen frequency signatures, each of which is the averaged power spectrum of the signal during 1/16 of a revolution. A larger or smaller number of frequency signatures may be used, but a limit on the former is the ability to generate a Fourier transform at reasonable cost in real time. The time signature of the compressor being inspected is compared point by point with the reference, and an acceptable device is within the limits depicted in FIG. 5 as dashed line curves on either side of the reference. At the same time, the frequency spectra of the compressor under test are compared, point by point, with the set of reference signatures of an acceptable device to determine if it is within limits or defective. One frequency signature is drawn to an enlarged scale in FIG. 7; reference data is available only for 4-25 KHz because other frequencies were filtered out. The limits of acceptability shown in this figure but not FIG. 6 are obtained from the test results of many good pumps.

A pump can be rejected in two planes, time and frequency. There are large number of reference points, for example, 1000 points in the time plane and 1000 points in the frequency plane. The test stand is operated by an unskilled employee, and the comparison with reference data is done automatically in the computer which displays to the operator that the unit passes or fails. The engineer or perhaps the repair stand employee examines the signatures of a rejected compressor and determines the nature and location of the defect. Abnormalities in vibration at a particular position of the moving device are located and identified, and corrective measures taken.

Figure 8:
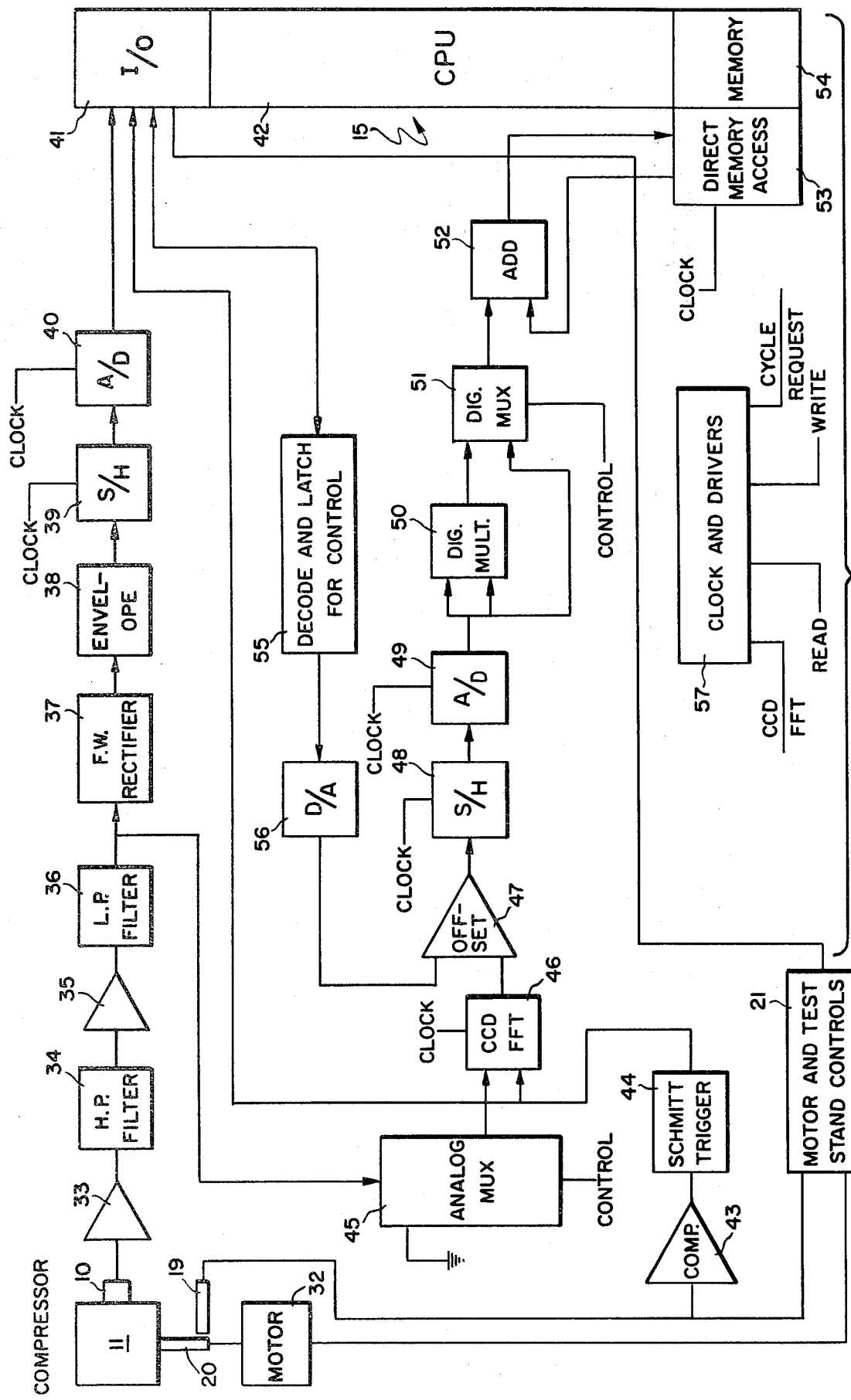
FIG. 8 is a block diagram of an illustrative embodiment of the compressor diagnostic system.

A more detailed description of a specific embodiment of the diagnostic system is given in connection with the detailed block diagram in FIG. 8. The vibration signal is generated by accelerometer 10, which is held against the pump 11 by pneumatic pressure. A motor 32 is coupled to the shaft 20 and the pump is driven in its normal operating direction. Data collection always starts at the same angular position and is averaged over sixteen complete revolutions. The signal is amplified by a preamplifier 33 and filtered by a high pass filter 34 (4000 Hz) located on the test stand driving the 30 feet or so of cable to the computer electronics package. This filter eliminates almost all of the factory generated noise which lies below 2000 Hz. The signal is boosted to a suitable level by amplifier 35 and filtered by an eight pole, low pass, 25 KHz, anti-aliasing filter 36. The output of this filter is the conditioned signal and is used for analysis in the time plane and the frequency plane.

For the time plane analysis, the conditioned signal is fed to a full wave rectifier 37 and hence to envelope detecting circuitry 38. The rectified signal is peak detected by a fast acquire, slower decay peak measuring circuit. The envelope is sampled at 1024 points during a revolution by sample-and-hold circuit 39, converted to a digital number by analog-to-digital converter 40 and channeled via Input/Output interface 41 to the central processing unit 42 of the computer. Sixteen revolutions are averaged point by point by a software program. The envelope of the signal gives a good idea of what is happening in the machine.

Sensor 19, which generates the position reference signal, is a magnetic pick-off that senses a longitudinal slot in the outer surface of the compressor shaft. The position reference signal is fed to a motor control 21, and to a comparator 43 which produces an output pulse when the magnitude of the positive-going signal rises above a reference. A Schmitt trigger 44 squares up the comparator pulse and feeds a once per revolution reference to I/O interface 41. This is used to synchronize the averaging of the data.

For the frequency plane analysis, the conditioned signal is passed through a computer controlled analog multiplexer 45. The output of the multiplexer (MUX) is analyzed by a charge coupled device fast Fourier device 46 such as that developed and sold by the Reticon Corporation of Sunnyvale, California. This unit does a complete 512 point transform in a few milliseconds covering the range of −25 KHz to +25 KHz. A complete transform can be done in a fraction of a revolution, real time, and thus each event such as valve operation can be analyzed separately. This has a distinct advantage over a single frequency analysis that covers one or more revolutions producing a mixing of all noise sources. The output of the CCD FFT 46 is an analog voltage which is quantized in time. The output voltage is proportional to the magnitude of the Fourier transform, however the voltage is superimposed on a DC bias. Since the averaged power spectrum is desired, the signal from the fast Fourier transform device 46 must be squared before it is averaged. The DC bias must be removed before the squaring or it will introduce an error into the power estimate.

This is accomplished as follows. The computer commands the analog multiplexer 45 to select the grounded input. In the fast Fourier transform device 46 the offset is calculated by computing the average value of the 512 points with the input grounded. The output voltage representing the offset passes through a differential amplifier 47, the signal is sampled by a sample-and-hold circuit 48, and converted to the digital equivalent by an analog-to-digital converter 49. The digitized offset bypasses a digital multiplier 50 and passes through a computer controlled digital multiplexer 51 to an adder 52 and hence to the direct memory access board 53 of the computer and is read into a memory 54. The offset value, it is noticed, passes straight through without being squared. The FFT offset is fed out of the I/O 41 to decode and latch circuitry 55 where it is stored and hence fed to a digital-to-analog converter 56. The digital equivalent of the offset is converted to an analog signal which is then subtracted from the real time analyzed data using differential amplifier 47. The offset is calculated for each pump before test data is taken. The drift during the short data collection period is insignificant. An alternative and probably preferable method is to keep and apply the offset in digital form.

Having determined and subtracted the offset, the output of amplifier 47 is a voltage proportional to the magnitude of the Fourier transform for 1/16 of a revolution. The FFT analog output is sampled and converted to a digital value (circuits 48 and 49). It is squared by the two-input digital multiplier 50 and the product is passed by digital multiplexer 51 to the two-input digital adder 52.

The adder output and one of its two inputs are connected to the computer memory 54 via the direct memory access board 53. Adder 52 is used to average the frequency data. This process is controlled by a clock 57 running at twice the data collection speed. This control controls alternate read and write cycles of the memory. A read cycle places the current contents of memory, the accumulated total for one point of the FFT, into one input of the adder. At the same time, one value of the squared FFT output is read into the other adder input. The two inputs are added and wait for the next clock cycle which writes the total into memory. For each revolution there are sixteen complete power spectra of 512 points for a total of 8192 data values. For example, there are sixteen values of power in the 10 KHz region, and so on. The FFT device gives values in the positive and negative plane, and corresponding pairs are added to reduce the number of data values to 4096. Each set of four data points is averaged, resulting in a final number of data points of 1024, the same as the time plane analysis. The clock and drivers 57 send alternate clock pulses to the CCD FFT 46 and to the A/D converters 40 and 49. The cycle request is made to memory to either read or write. The A/D circuits sample at one-half the rate the cycle request goes to memory.

Computer system 15 is typically a Digital Equipment Corporation PDP 11/23 minicomputer. After summing all of the data values at every reference point for sixteen revolutions, a division is performed to get the average. The data points of the compressor under test are compared with the reference data of an acceptable compressor to determine if predetermined limits are exceeded. This is done point by point for the 1024 points in the time plane and the 1024 points in the frequency plane. If there are enough data points that exceed the acceptable limits, a red light is turned on and indicates to the operator that the compressor is a reject. The number of above-limit data points needed to reject a pump depends on how tight the engineer wants the tolerances to be. Defective pumps are taken apart at the repair stand to see what is wrong. The computer system may provide a hard copy graphic display to pinpoint more precisely what the defect is and its location.

This automated diagnostic system and method of inspecting moving devices for internal defects is fast, uses only one test station, is more sensitive than a human operator, eliminates variations in judgment, and finds some defects not found by conventional testing. The frequency is not restricted to the audio and above-audio range and extends to ultrasonics.

While the invention has been particularly shown and described with reference to preferred embodiments thereof, it will be understood by those skilled in the art that the foregoing and other changes in form and details may be made therein without departing from the spirit and scope of the invention.

The invention claimed is:

1. A nonintrusive method of detecting internal defects in moving devices which have repetitive movements comprising:
   generating a sensor signal corresponding to the vibrations of said device during at least one cycle of movement;
   analyzing said sensor signal in real time to produce a time signature related to device position that is the envelope of said signal, and to produce a set of frequency signatures related to device position that are the separate power spectra for fractions of a cycle; and
   comparing said signatures with those of an acceptable device to identify abnormalities in vibration.

2. The method of claim 1 wherein said signatures are averaged over a predetermined number of cycles.

3. The method of claim 1 wherein said sensor signal is conditioned prior to time and frequency analysis by high pass filtering to eliminate extraneous noise and low pass filtering for anti-aliasing.

4. A nonintrusive method of detecting internal defects in rotary devices which have repetitive movements comprising:
   sensing the vibrations of said device during a designated number of revolutions and generating a sensor signal;

conditioning said sensor signal to extract low frequency extraneous noise and high frequencies that could result in aliasing errors;

generating a position reference in each revolution to synchronize averaging;

producing a time signature which is the averaged envelope of said conditioned signal;

producing a set of frequency signatures which are separately calculated and are the averaged power spectra of said conditioned signal for equal fractions of a revolution; and comparing said time and frequency signatures with reference data of an acceptable device and statistically derived limits of acceptability to identify abnormalities in vibration at a particular position of the rotating device.

5. The method of claim 4 wherein said conditioned signal has a frequency band of about 4–25 kilohertz.

6. The method of claim 4 wherein said position reference is generated by sensing the position of the shaft of said rotary device.

7. The method of claim 4 wherein a fast Fourier transform is performed and the output squared to yield each power spectra.

8. The method of claim 7 wherein the DC offset of the output of said fast Fourier transform is determined and subtracted prior to squaring.

9. An acoustical defect detecting system for inspecting moving devices which have repetitive movements comprising:

a sensor which generates an electrical signal representative of the vibrations of said device;

first means for producing a time signature which is related to device position and is the envelope of said signal during at least one cycle of movement of said device;

second means for producing a set of frequency signatures that are related to device position and are each the power spectrum of said signal during a fraction of one cycle of movement; and means for comparing said signatures with those of an acceptable device to identify internal defects.

10. The system of claim 9 wherein said second means has a fast Fourier transform device and a multiplier which squares its output.

11. An acoustical defect detecting system for inspecting rotary devices such as compressors which have repetitive movements comprising:

a sensor which generates an electrical signal representative of the vibrations of said device;

means for conditioning said signal to filter out low frequency noise and high frequencies that could result in aliasing errors;

means for generating a position reference once per revolution to synchronize averaging;

first analysis means for producing a time signature which is the averaged envelope of said conditioned signal over a designated number of revolutions;

second analysis means for producing a set of frequency signatures that are the averaged and separately calculated power spectra of said conditioned signal during fractions of a revolution; and means for comparing said time and frequency signatures with statistically derived reference data of an acceptable device to identify internal defects at a particular position of said device.

12. The system of claim 11 wherein said position reference generating means is comprised of a magnetic sensor which senses the position of the shaft of said rotary device, and means which includes a comparator and Schmitt trigger for generating one pulse per revolution.

13. The system of claim 11 wherein said first analysis means has a rectifier and a peak follower.

14. The system of claim 13 wherein said second analysis means has a fast Fourier transform device and means for squaring its output to yield each power spectra.

15. The system of claim 14 and means for determining the DC offset of the output of said fast Fourier transform device and subtracting said offset.

* * * * *